Figure 1:
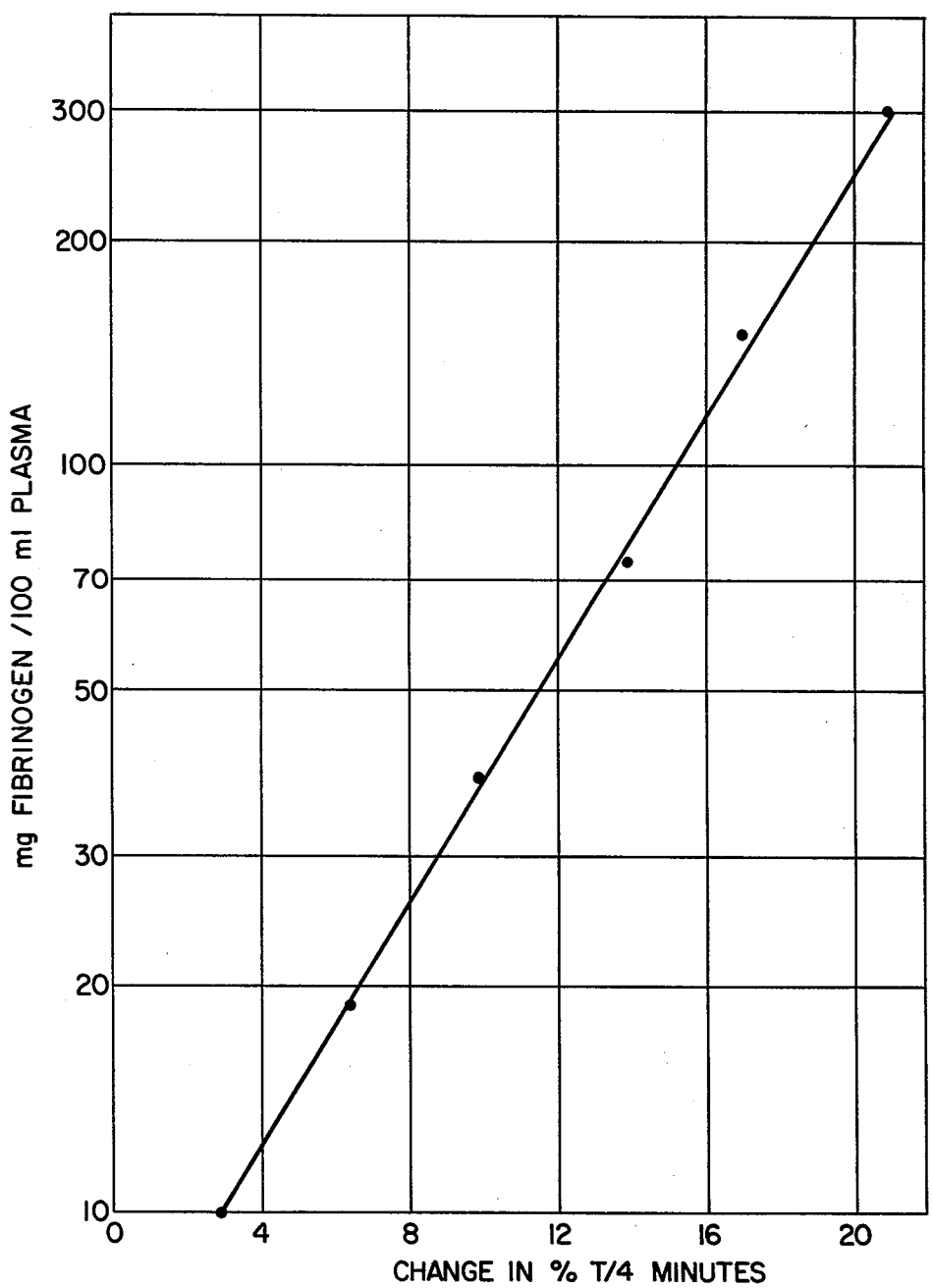

United States Patent [19]

Babson

[11] 4,205,954

[45] Jun. 3, 1980

[54] KINETIC LATEX AGGLUTINOMETRY

[75] Inventor: Arthur L. Babson, Chester, N.J.

[73] Assignee: Warner-Lambert Company, Morris Plains, N.J.

[21] Appl. No.: 910,060

[22] Filed: May 26, 1978

[51] Int. Cl.² .................. G01N 21/24; G01N 33/16
[52] U.S. Cl. .................. 23/230 B; 250/574; 356/339; 356/433; 424/12
[58] Field of Search .................. 23/230 B; 424/12; 250/574

[56] References Cited

U.S. PATENT DOCUMENTS

| | | | |
|---|---|---|---|
| 3,551,555 | 12/1970 | Schuurs | 424/12 |
| 3,781,414 | 12/1973 | Huber | 424/12 |
| 3,873,683 | 3/1975 | Fishbein | 424/12 |
| 3,905,767 | 9/1975 | Morris | 250/574 |
| 3,967,901 | 7/1976 | Rodriguez | 250/574 X |
| 4,118,192 | 10/1978 | Sawai | 422/56 |

OTHER PUBLICATIONS

Chemical Abstracts, 85:121538v (1976).
R. P. Tengerdy et al., Nature, 210, 708 (May 14, 1966).
Chemical Abstracts, 81:148042h (1974).

*Primary Examiner*—Sidney Marantz
*Attorney, Agent, or Firm*—Stephen I. Miller; Stephen Raines; Albert H. Graddis

[57] ABSTRACT

An immunoassay wherein the sample containing an immunologic substance is added to a suspension of particles coated with a second immunologic substance which is specific to the immunologic substance of the sample. The change in percentage of light transmission through the suspension undergoing the resulting agglutination is measured for a predetermined period of time and compared to a standard graph. The suspension is under constant agitation during the measurement.

3 Claims, 3 Drawing Figures

KINETIC LATEX AGGLUTINOMETRY

Prior to the new and novel technique disclosed herein, quantitative immunoassay techniques have fallen into a hierarchy of sensitivities in which precipitin reactions have shown the least sensitivity and radioimmunoassays have the greatest sensitivities.

Precipitin reactions in antibody containing gels whether employing unidirectional diffusion in columns as in the Oudin Agar Column Procedure (Oudin, 1946, Compt. Rend. Acad. Sci. 222, 115) or the Mancini radial immunodiffusion procedure (Mancini, G., A. O. Carbonara and J. F. Heremans, Immunochemical Quantitation of Antigens by Single Radial Immunodiffusion. Immunochemistry 2:235-254 (1965) have the further disadvantage of being slow and providing poor quantitation of the antigenic component. Quantitation and speed are somewhat improved with the Laurell technique (Laurell, C. B., Quantitative Estimation Of Proteins By Electrophoresis in Agarose Gel Containing Antibodies Anal. Biochem. 15: 45-52 (1966)) in which the reaction is carried out under the influence of an electric field, i.e., immunoelectrophoresis, however, the technique requires sophisticated equipment specifically designed for this procedure.

Precipitin rections have also been quantitated in solution after reaction of polyvalent antigens with specific antibody by nephalometric (Killingsworth, L. M. and J. Savory, Nephalometric studies of the precipitin reaction: a model system for specific protein measurements, Clin. Chem. 19:403 (1973)) or turbidimetric measurement. A kinetic measurement of the precipitin reaction has also been described (Buffone, A. J. J. Savory, R. E. Cross, and J. E. Hammont, Evaluation of Kinetic Light Scattering As An Approach To the Measurement Of Specific Proteins With The Centrifugal Analyzer, I. Methodology Clin. Chem. 21:1731 (1975)) as a means to quantitate immunoglobulins.

There are a number of disadvantages in the precipitin reactions. Besides lacking sensitivity, precipitin reactions in solutions are only valid over a discrete concentration range as either an antigen or antibody excess will cause what is known as the Ehrlich prozone phenomenon in which the precipitin reaction does not occur. All solutions required for the reaction must also be perfectly clear since any traces of turbidity or cloudiness may obscure the results.

Attaching antibodies to solid support systems such as latex particles or erythrocytes enhances the sensitivity of the reaction 100-1000 fold when compared to the precipitin reaction and avoids the prozone phenomenon when there is an excess of antibody present.

Agglutination reactions of this type are basically qualitative procedures. Agglutination reactions using latex particles have only been quantitated by a technique known as differential light scattering (Blume, P. and L. J. Greenberg, Application of Differential Light Scattering To The Latex Agglutination Assay For Rheumatoid Factor. Clin. Chem. 21: 1234 (1975)). The Blume technique, however, requires a polarizing lazer light source and very sophisticated detection devices to measure the intensity of scattered light of the various angles of scatter. The equipment and technology required to quantitate agglutination reactions in this manner, however, make the procedures not economically feasible for the small to medium size clinical laboratory.

I have discovered that in dilute suspension and under constant agitation, the rate of aggregation of antibody-coated particles as measured by increases in light transmission is a function of antigen concentration. Using the technique of my discovery, I have further found that it provides a quantitative determination of antigen concentration with about a 10 fold increase in sensitivity over the slide agglutination technique.

An object of this invention is, therefore, the description of my new method in which the rate of change of light transmission in a dilute suspension of antibody-coated particles under constant agitation is shown to be a function of antigen concentration.

A further object of this invention is the description of my new method in the quantitation of polyvalent antigens.

Another object of this invention is the description of my new method in which the rate of change of light transmission in a dilute suspension of antigen coated particles under constant agitation is shown to be a function of antibody concentration.

Yet a further object of this invention is the description of my new method in the quantitation of antibody.

Among the polyvalent antigens which are easily quantitated at low concentrations using my method are various coagulation factors such as fibrinogen, fibrinogen degradation products, factor VIII antigen, antithrombin III, plasminogen, and platelet factor 4; various serum proteins such as immunoglobulin G, immunoglobulin A, immunoglobulin M, $\alpha$-Antitrypsin, $\beta$-lipoprotein, $\alpha_2$-macroglobulin, thyroxine-binding globulin, C'3 complement, transferrin, ceruloplasmin, haptoglobulin, and human placental lactogen; various urinary proteins such as human chorionic gonadotropin and Bence Jones protein.

Among the antibodies which are easily quantitated at low concentrations using my method with antigen coated particles are antistreptolysin O, rheumatoid factor and antinuclear antibody.

As particles used to bind and carry the antigen or antibody molecules, there can be used any compatible material such as glass, clay, red blood cells, or polystyrene latex particles; these materials being known in the art. Of these materials, polystyrene latex particles having a particle size of between about 0.15 to 0.9 microns are preferred for their ease of use.

It is believed that one of ordinary skill in the art can, utilizing the description contained herein, utilize the method of the present invention to its fullest extent in immunological quantitative and qualitative assays for various antigen and antibody systems. The following specification embodiments are, therefore, to be simply construed as merely illustrative and not to limit the remainder of the specification and claims whatsoever.

EXAMPLE 1

Fibrinogen Assay

Rabbit Anti-Human Fibrinogen was prepared and adsorbed on latex particles in accordance with the procedure set forth in U.S. Pat. No. 4,003,988 (the only difference being that the rabbits used to produce the antibody were presensitized to fibrinogen, not HCG as in the patent disclosure).

The assay was performed on a Chronolog Platelet Aggregometer using the following parameters:

(1) The recorder used in conjunction with the aggregometer was adjusted to a 5 mv span (less than 5 mv was found to give extraneous noise; greater than 5 mv reduced sensitivity) and a chart speed of 0.5 inches per minute.

(2) The latex was diluted 1:80 in a piperazine buffer (prepared as in U.S. Pat. No. 4,003,988) and the recorder was set to read 0% T at this dilution. A dilution of 1:160 of latex in buffer was used to calibrate the recorder to register 100% T. Although other dilutions are not excluded, these specific dilutions were chosen as giving a satisfactory degree of sensitivity in the particular instrument used in this series of tests.

(3) Constant minimum stirring of the test reaction mixture was maintained in the aggregometer cuvette with a teflon stir bar.

The test was performed by placing 1 ml of the latex dilution in an aggregometer cuvette and warming the cuvette to 37° C. The Antigen-Antibody reaction was initiated with 50 µl of plasma diluted 1:100 in saline.

FIG. 1 shows the relationship of fibrinogen concentration in plasma to the change in percent transmission ($\Delta\%$ T) in four minutes. A good dose response is evident between 10 and 300 mg fibrinogen per 100 ml in the undiluted plasma.

EXAMPLE 2

FDP Assay

The excellent sensitivity of the assay for fibrinogen in plasma (FIG. 1) suggested its use as a quantitative assay for fibrinogen degradation products (FDP) in serum.

Normal plasma was serially diluted in serum. FDP sensitized Latex prepared in similar manner as in U.S. Pat. No. 4,003,988, was diluted 1:50 in the piperazine buffer of Example 1, and the reaction initiated by mixing 1 ml with 25 µl of serum.

Figure 2:
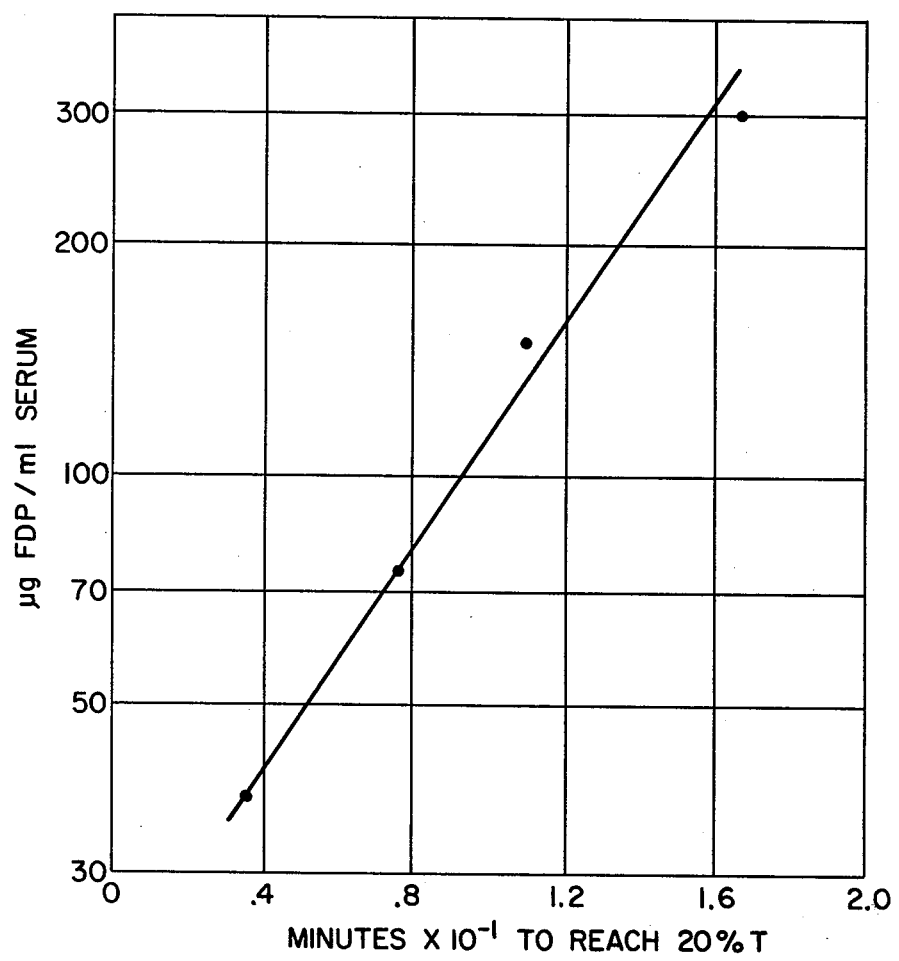

FIG. 2 shows the dose response between 30 and 300 µg of FDP per ml of serum. In the assay the reciprocal (i.e. $10^{-1}$) of the time that was required to reach 20% T was used as the standard of measurement.

EXAMPLE 3

HCG Assay

Figure 3:
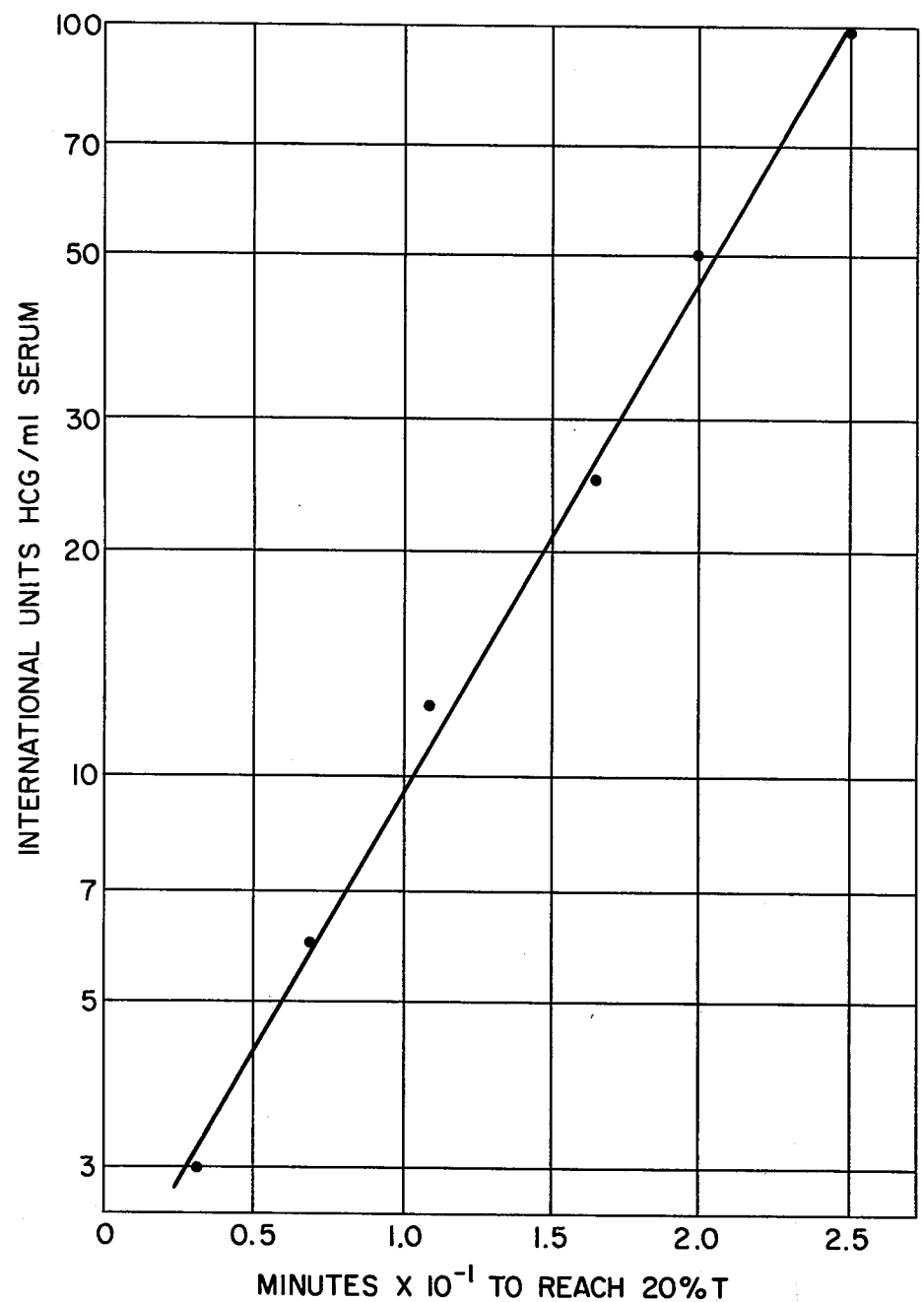

A human chorionic gonadotropin assay in serum using the same conditons as in Example 2 gave a dose response curve between 3 and 100 units per ml as illustrated in FIG. 3.

Using this procedure which I have termed kinetic latex agglutinometry an unknown quantity of an antigen, or antibody if the sensitized latex particles carried the antigen, can easily be determined by assaying and comparing the results obtained against such standard curves as shown in the figures. Such a technique has several advantages over other immunoassay procedures, including latex agglutination on a slide, for example; it is a homogenous procedure requiring only a single stable reagent.

From the foregoing descriptions, one skilled in the art can easily ascertain the essential characteristics of the invention and without departing from the spirit and scope thereof can make various changes and/or modifications to the invention for adapting it to various usages and conditions. Accordingly, such changes and modifications are properly intended to be within the full range of equivalents of the following claims:

I claim:

1. In a method for the detection and quantification of an antigen or antibody which comprises the addition of a sample containing a quantity of an antigen or antibody to a suspension kept under constant agitation of the reactive antigen or antibody coated particles and allowing this antigen-antibody coated particle reaction suspension or antibody-antigen coated particle reaction suspension to agglutinate thereby indicating the presence of a specific antigen or antibody in the sample, the improvement comprising measuring the change in percentage of light transmission through the reaction suspension for a predetermined period of time and comparing the change in percent transmission to a standard graph indicating percent transmission for the same predetermined time period for varying quantities of antigen or antibody.

2. The method of claim 1 which comprises antibody-coated particles of latex.

3. The method of claim 1 which comprises antigen-coated particles of latex.

* * * * *